US00PP26348P2

(12) United States Plant Patent
Hilst

(10) Patent No.: US PP26,348 P2
(45) Date of Patent: Jan. 26, 2016

(54) ***RHODOHYPOXIS* PLANT NAMED 'HIL2008-02'**

(50) Latin Name: ***Rhodohypoxis* hybrid**
Varietal Denomination: Hil2008-02

(71) Applicant: Philip van Hilst, Kaatsheuvel (NL)

(72) Inventor: Philip van Hilst, Kaatsheuvel (NL)

( * ) Notice: Subject to any disclaimer, the term of this patent is extended or adjusted under 35 U.S.C. 154(b) by 93 days.

(21) Appl. No.: 13/999,147

(22) Filed: Jan. 21, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of *Rhodohypoxis* named 'Hil2008-02', that is characterized by its flowers that are bright red-pink in color, its vigorous growth habit, and its long blooming habit.

2 Drawing Sheets

Botanical classification: *Rhodohypoxis* hybrid.
Cultivar designation: 'Hil2008-02'.

BACKGROUND OF THE INVENTION

The present invention relates to a new and distinct cultivar of *Rhodohypoxis* plant of hybrid origin, botanically known as *Rhodohypoxis* 'Hil2008-02' and will be referred to hereafter by its cultivar name, 'Hil2008-02'.

The Inventor selected the new cultivar as a unique seedling in 2005 in Kaatsheuvel, The Netherlands. The seedling arose from seeds sown from a mixture of seed collected and pooled from unnamed plants of hybrid *Rhodohypoxis*.

Asexual propagation of the new cultivar was first accomplished by root cuttings in in Kaatsheuvel, The Netherlands in 2006 by the Inventor. Asexual propagation by root cuttings has determined that the characteristics of the new cultivar are stable and are reproduced true to type in successive generations.

SUMMARY OF THE INVENTION

The following traits have been repeatedly observed and represent the characteristics of 'Hil2008-02'. These attributes in combination distinguish 'Hil2008-02' a new and distinct cultivar of *Rhodohypoxis*.

1. 'Hil2008-02' exhibits flowers that are bright red-pink in color.
2. 'Hil2008-02' exhibits a vigorous growth habit.
3. 'Hil2008-02' exhibits a long blooming period.

The new cultivar can be compared to the *Rhodohypoxis* ×*rhodoxis* cultivars 'Hebron Farm Cerise' (not patented) and 'Hebron Farm Alba' (not patented). Both cultivars differ from 'Hil2008-02' in having a less vigorous growth habit and in having a shorter bloom period. In addition, 'Hebron Farm Cerise' differs from 'Hil2008-02' in having light pink flowers and 'Hebron Farm Alba' differs from 'Hil2008-02' in having white flowers.

BRIEF DESCRIPTION OF THE DRAWINGS

The accompanying colored photographs illustrate the overall appearance and distinct characteristics of the new *Rhodohypoxis*. The photographs were taken of a six month-old plant of 'Hil2008-02' as grown outdoors in a 12-cm container in Kaatsheuvel, The Netherlands.

The photograph in FIG. 1 provides a side view of 'Hil2008-02' in bloom.

Figure 1:
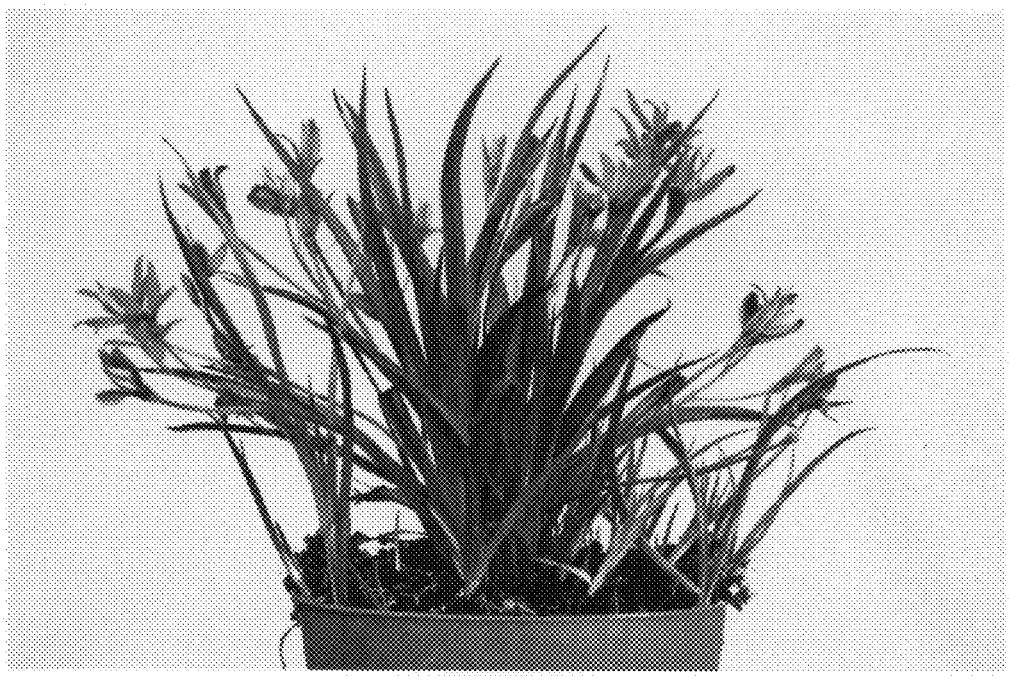
Figure 2:
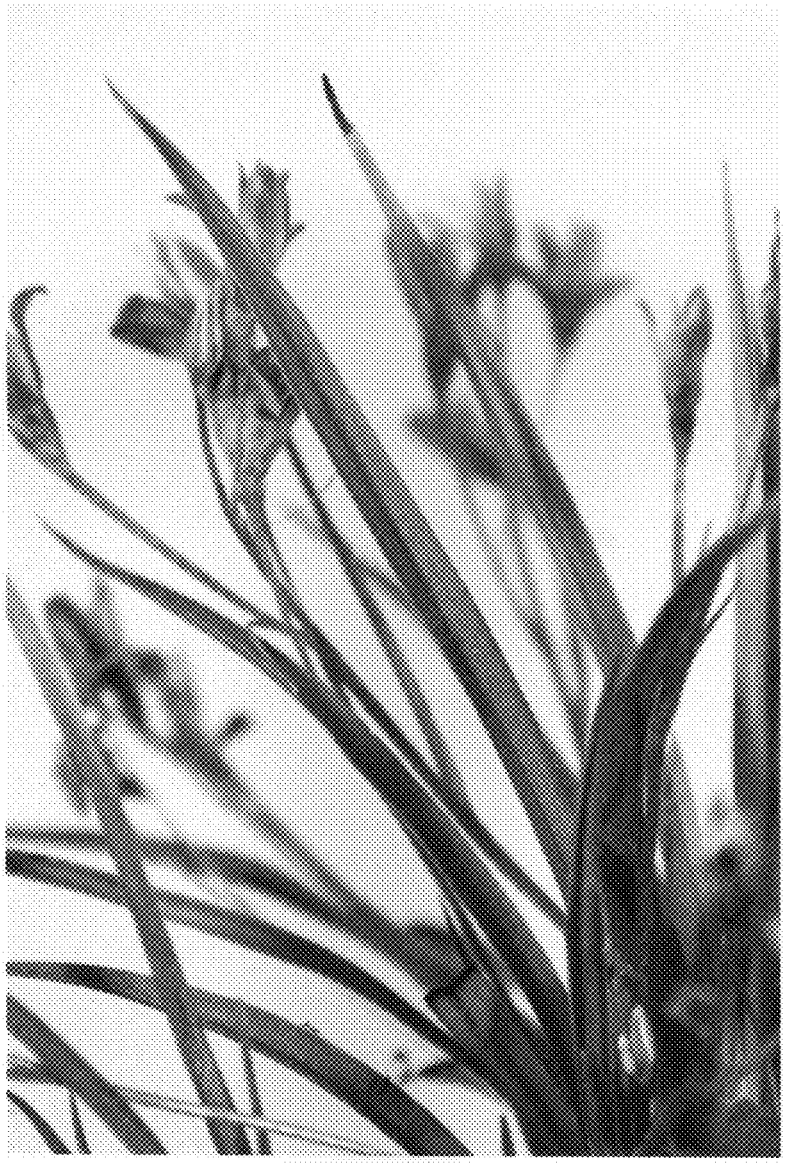

The photograph in FIG. 2 provides a close-up view of the leaves of 'Hil2008-02'.

The colors in the photographs are as close as possible with the digital photography and printing techniques utilized and the color codes in the detailed botanical description accurately describe the new *Rhodohypoxis*.

DETAILED BOTANICAL DESCRIPTION OF THE PLANT

The following is a detailed description of a six-month-old plant of the new cultivar as grown outdoors in a 12-cm container in Kaatsheuvel, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Early summer to early autumn in the Netherlands.

*Plant habit*.—Herbaceous perennial, compact grass-like foliage with inflorescences growing from the leaf-axils.

*Height and spread*.—Reaches about 13.6 cm in height and 23.8 cm in spread.

*Hardiness*.—At least in U.S.D.A. Zone 8.

*Diseases and pests*.—Not more susceptible to pests and diseases than other *Rhodohypoxis* varieties.

*Root description*.—Fleshy and fibrous.

*Rhizomes*.—Tuberous, 3 cm in length, 2 mm in width, color a blend of N200C/200C.

*Propagation*.—Root cuttings.

*Growth rate*.—Vigorous in comparison to other cultivars.

*Stem description*.—No lateral branches present, only basal clumps.

Foliage description:

*Leaf shape*.—Linear, carinate.

*Leaf division*.—Simple.

*Leaf base*.—Decurrent.

*Leaf apex*.—Long acuminate.

*Leaf venation*.—Longitudinal, parallel, not prominent, same color as leaves.

*Leaf margins*.—Entire.

*Leaf attachment*.—Petiolate.

*Leaf arrangement*.—Clump (basal).

*Leaf orientation*.—Held primarily upright.

*Leaf surface*.—Glabrous to slightly glossy, margins and veins on lower surface moderately covered with soft thin hairs, 2 mm in length and NN155C to NN155D.

*Leaf color*.—Young leaves (upper and lower surface); 143B, mature leaves (upper and lower surface); 137B.

*Leaf size*.—Average of 13.8 cm in length and 7 mm in width.

*Leaf quantity* .—Average of 14 leaves per clump.

Flower description:

*Inflorescence type*.—Solitary.

*Inflorescence size*.—Average of 5.1 cm in width and 6.5 cm in depth.

*Lastingness of flowers*.—About 1 week.

*Flower size*.—An average of 1.6 cm in depth and 3 cm in diameter.

*Flower fragrance*.—Faint, sweet and pleasant.

*Flower number*.—4 per inflorescence, 8 per clump.

*Flower form*.—Rotate, single.

*Flower opening rate*.—50% of the flowers open at one stage.

*Flower aspect*.—Upright.

*Flower bud*.—Linear to oblong in shape, an average of 1.3 cm in length and 3 mm in width, color; 64B, ribbed with 148A.

*Tepal number*.—Average of 6.

*Tepal shape*.—Lanceolate.

*Tepal margin*.—Entire.

*Tepal size*.—Average of 1.6 cm in length, three inner tepals average of 6 mm in width, three outer tepals an average of 3 mm in width.

*Tepal aspect*.—Upright and slightly spreading.

*Tepal surface*.—Glabrous and velvety on upper and lower surface.

*Tepal apex*.—Narrowly acute on three inner tepals, broadly acute on three outer tepals.

*Tepal base*.—Cuneate.

*Tepal color*.—When opening upper surface; 61B, when opening lower surface; three inner tepals 68C to 68D, three outer tepals 146D with margins 70B, when fully open lower surface; three inner tepals 68C to 68D, three outer tepals 146D with margins 70B, all fading to 70B.

*Calyx*.—Average of 1.6 cm in length and 3 cm in diameter, rotate in shape.

*Peduncles*.—An average of 10.9 cm in length, peduncle flattened with an average diameter at the widest point 2 mm, at the most narrow point 1.5 mm, strength is very strong, average angle of 50° to soil level and 143A in color.

*Pedicels*.—An average of 2.5 cm in length and 1 mm in diameter, strong in strength, held at an average angle of 30° and 146A to 146B in color.

Reproductive organs:

*Gynoecium*.—No pistils present.

*Androecium*.—Stamens; 6, anthers; 2 mm in length and 13A in color; filament; 1 mm in length and 187C in color, pollen; moderate in quantity and 12A in color.

*Fruit/seeds*.—None are produced, sterile.

It is claimed:

1. A new and distinct cultivar of *Rhodohypoxis* plant named 'Hil2008-02' as herein illustrated and described.

* * * * *